United States Patent
Hamaguchi et al.

(10) Patent No.: US 9,205,206 B2
(45) Date of Patent: Dec. 8, 2015

(54) INHALER AND INHALER MOUTHPIECE

(75) Inventors: Takehiro Hamaguchi, Kyoto (JP); Shinya Tanaka, Osaka (JP); Satoshi Kurata, Kyoto (JP); Hideyuki Kobayashi, Osaka (JP)

(73) Assignee: OMRON Healthcare Co., Ltd., Kyoto (JP)

( * ) Notice: Subject to any disclaimer, the term of this patent is extended or adjusted under 35 U.S.C. 154(b) by 1457 days.

(21) Appl. No.: 12/088,628

(22) PCT Filed: Sep. 13, 2006

(86) PCT No.: PCT/JP2006/318153
§ 371 (c)(1),
(2), (4) Date: Mar. 28, 2008

(87) PCT Pub. No.: WO2007/040025
PCT Pub. Date: Apr. 12, 2007

(65) Prior Publication Data
US 2010/0147292 A1    Jun. 17, 2010

(30) Foreign Application Priority Data
Oct. 4, 2005   (JP) ................. 2005-291462

(51) Int. Cl.
*A61M 11/02* (2006.01)
*A61M 15/00* (2006.01)

(52) U.S. Cl.
CPC ............ *A61M 11/02* (2013.01); *A61M 15/00* (2013.01); *A61M 15/0021* (2014.02)

(58) Field of Classification Search
CPC ............... A61M 15/00; A61M 2015/0013; A61M 2015/0015; A61M 2015/0016; A61M 2015/0018; A61M 2015/002; A61M 2015/0021; A61M 11/00–11/08
USPC ............ 128/200.14–200.23, 203.12, 204.14, 128/206.21, 207.14; 239/102.1, 102.2, 338, 239/370; 222/196, 630, 635, 637
See application file for complete search history.

(56) References Cited

U.S. PATENT DOCUMENTS 5,415,161 A * 5/1995 Ryder .................. 128/200.23
5,497,764 A * 3/1996 Ritson et al. ............. 128/200.14
(Continued)

FOREIGN PATENT DOCUMENTS

| | | |
|---|---|---|
| GB | 2333236 | 7/1999 |
| JP | 04-095046 | 8/1992 |

(Continued)

OTHER PUBLICATIONS

RU patent application No. 2008117423, Decision on Grant mailed Sep. 10, 2009.
(Continued)

*Primary Examiner* — Justine Yu
*Assistant Examiner* — LaToya M Louis
(74) *Attorney, Agent, or Firm* — Weaver Austin Villeneuve & Sampson LLP

(57) ABSTRACT

A mouthpiece (150A) has an aerosol lead-out flow passage (104), an aerosol lead-out opening (105), and exhalation discharge openings (106). The lead-out flow passage (104) includes a first flow passage (104A) extending upward, a second flow passage (104B) extending obliquely forward from the first flow passage (104A), and a corner flow passage (104C) for connecting the first flow passage (104A) and second flow passage (104B) of the lead-out flow passage (104). The mouthpiece (150A) has a curvature portion (153) formed by curving that portion of the first flow passage (104A) wall surface which crosses the center line of the first flow passage (104A). The exhalation discharge openings (106) are provided in a wall surface defining the second flow passage (104B), at a position circumferentially displaced from the wall surface portion at which the curvature portion (153) is provided. In the mouthpiece and an inhaler with the mouthpiece, although an exhalation valve and, in addition, an inhalation valve are eliminated, leakage of aerosol from a pressure regulation opening and the exhalation opening is prevented irrespective of usage manners.

5 Claims, 11 Drawing Sheets

(56) References Cited

U.S. PATENT DOCUMENTS

| | | | |
|---|---|---|---|
| 6,129,080 A * | 10/2000 | Pitcher et al. | 128/200.21 |
| 6,131,568 A * | 10/2000 | Denyer et al. | 128/200.21 |
| 6,513,519 B2 * | 2/2003 | Gallem | 128/200.14 |
| 6,615,826 B1 * | 9/2003 | Gabrio et al. | 128/200.23 |
| 6,708,690 B1 * | 3/2004 | Hete et al. | 128/204.18 |
| 7,270,123 B2 * | 9/2007 | Grychowski et al. | 128/200.14 |
| 7,677,467 B2 * | 3/2010 | Fink et al. | 239/8 |
| 7,849,851 B2 * | 12/2010 | Zierenberg et al. | 128/200.14 |
| 2003/0062047 A1 * | 4/2003 | O'Rourke | 128/205.24 |
| 2004/0244794 A1 * | 12/2004 | Richards | 128/203.15 |
| 2006/0065267 A1 * | 3/2006 | Tran et al. | 128/200.14 |
| 2006/0150971 A1 * | 7/2006 | Lee et al. | 128/203.15 |
| 2006/0243274 A1 * | 11/2006 | Lieberman et al. | 128/200.14 |
| 2007/0272235 A1 * | 11/2007 | Miyamoto | 128/200.14 |

FOREIGN PATENT DOCUMENTS

| | | |
|---|---|---|
| JP | 05-337183 | 12/1993 |
| JP | 11-276587 | 10/1999 |
| JP | 2004-290592 | 10/2004 |
| RU | 44510 | 3/2005 |
| WO | 94/16759 | 8/1994 |

OTHER PUBLICATIONS

EP patent application No. 06797903.9, Supplemental European Search Report mailed Jul. 22, 2011.
JP patent application No. 2005-291462, Decision to Grant Patent mailed May 17, 2011.
RU patent application No. 2008117423, Official Action mailed Apr. 23, 2009.

* cited by examiner

FIG.4

⇐ OUTSIDE AIR
⬅ AEROSOL
← EXHALATION
⇐--- COMPRESSED AIR
    (OUTSIDE AIR)

⇐ OUTSIDE AIR
← AEROSOL

→ AEROSOL
← EXHALATION

← AEROSOL
⇐ OUTSIDE AIR

FIG.20

← AEROSOL
← EXHALATION

← AEROSOL
← EXHALATION

INHALER AND INHALER MOUTHPIECE

TECHNICAL FIELD

The present invention relates to an inhaler ejecting aerosol generated in an aerosol generation portion through an aerosol lead-out portion, and an inhaler mouthpiece for use in the same as an aerosol lead-out portion.

BACKGROUND ART

An inhaler is an apparatus used for disinfection, treatment and the like of bronchi and is in widespread use in medical institutions and at home as treatment equipment for treating respiratory disease such as bronchitis or asthma. In particular, an inhaler ejecting atomized chemical solution for the treatment purpose is called inhalation treatment equipment.

Inhalers may mainly be classified, according to the atomization principles, into three categories: compressor-type inhalers, ultrasonic-type inhalers, and ultrasonic-mesh-type inhalers. A compressor-type inhaler is an inhaler which generates spray particles by mixing liquid to be atomized into compressed air delivered from a compressor and then causing the compressed air including the liquid to impinge on a wall called a baffle to scatter the liquid. A ultrasonic-type inhaler is an inhaler which forms liquid into spray particles by driving an ultrasonic element to apply high-frequency vibration to liquid and using cavitation generated by this high-frequency vibration. A ultrasonic-mesh-type inhaler is an inhaler which forms spray particles by supplying liquid between a vibration element and a mesh member arranged to oppose each other and driving the vibration element in this state to provide vibration to the liquid, allowing the liquid to pass through holes provided in the mesh, thereby pulverizing the liquid.

An inhaler generally includes an apparatus body including an aerosol generation portion and an aerosol lead-out portion. The aerosol generation portion is a part that generates aerosol by atomizing liquid into spray particles and applying this spray particles to the introduced outside air. On the other hand, the aerosol lead-out portion is a part that ejects the generated aerosol to the oral cavity or nasal cavity of a user, and employs a mouthpiece, a nosepiece, a mask or the like.

The aerosol generation portion is provided with a pressure regulation opening for regulating the internal pressure inside of aerosol (an auxiliary outside air introduction opening for introducing the outside air into the apparatus body in an auxiliary manner when a user performs an exhalation operation), and the aerosol lead-out portion is provided with an aerosol lead-out opening for leading the generated aerosol out. In addition, the aerosol lead-out portion is provided with an exhalation discharge opening for discharging the breath exhaled by the user to the outside. Usually, among these openings provided for the apparatus body, the pressure regulation opening and the exhalation discharge opening have respective check valves attached thereto to close the respective openings. Each of these check valves is provided to allow the user to breathe smoothly without suffocation and also to inhale aerosol efficiently. The check valve provided for the pressure regulation opening is generally called an inhalation valve, and the check valve provided for the exhalation discharge opening is generally called an exhalation valve.

There are mainly two usage manners as manners of using an inhaler with a mouthpiece. In one of the usage manners, a user puts a mouthpiece into the mouth, and this usage manner is intended for users having relatively large vital capacity of the lung. In this usage manner, the check valve function of the aforementioned inhalation valve and exhalation valve advantageously allows the user to inhale the generated aerosol with almost no loss. In the other usage manner, a user confronts a mouthpiece to take in aerosol ejected from the mouthpiece without putting the mouthpiece into the mouth, and this usage manner is intended for users having relatively small vital capacity of the lung. Although this usage manner disadvantageously causes much loss of the generated aerosol as compared with the aforementioned usage manner of putting the mouthpiece into the mouth, it is an effective manner in that even infants or elderly people having small vital capacity of the lung can use inhalers relatively easily. Here, even in this usage manner of not putting the mouthpiece into the mouth, the generated aerosol can be ejected from the aerosol lead-out opening with almost no loss, because of the check valve function of an inhalation valve and an exhalation valve. However, since the user does not put the mouthpiece into the mouth, all of the ejected aerosol is not taken in by the user, and in this respect, the loss of aerosol is increased.

In designing inhalers, it is important to consider that aerosol can be inhaled efficiently by users, whichever of these usage manners is employed. Nevertheless, from a hygiene stand point, inhalers require cleaning and disinfection operations after use by disassembling the apparatus body, so that it is also important to simplify the apparatus configuration as much as possible to facilitate disassembly and assembly operations. If the apparatus configuration can be simplified, provision of inhalers at low costs become possible, accordingly.

In particular, unlike the other components, the inhalation valve and the exhalation valve are formed of flexible members, are thus difficult to handle, and in addition, are likely to be broken or lost during disassembly and assembly operations, and therefore their elimination is favorable. However, with the mere elimination of the inhalation valve and/or the exhalation valve, much precious aerosol leaks out from the pressure regulation opening and the exhalation discharge opening, thereby significantly reducing the inhalation efficiency.

Then, an inhaler and an inhaler mouthpiece are known as disclosed in Japanese Utility-Model Laying-Open No. 4-95046 (Patent Document 1) and Japanese Patent Laying-Open No. 5-337183 (Patent Document 2), in which the apparatus configuration is simplified by eliminating an exhalation valve, while loss of aerosol (here, mainly, leakage of aerosol from an exhalation discharge opening during inhalation) which may be caused by eliminating an exhalation valve is reduced as much as possible.

FIG. 21 is a longitudinal cross-sectional view of an inhaler mouthpiece disclosed in the above-noted Patent Document 1, and FIG. 22 is a front view as viewed from arrow XXII shown in FIG. 21. As shown in FIG. 21 and FIG. 22, an inhaler mouthpiece 250 disclosed in the above-noted Patent Document 1 includes an inhalation portion 252 having openings at opposite ends and an introduction portion 251 having an opening at one end and communicating with an aerosol generation portion at the other end, and is structured such that introduction portion 251 is inserted into inhalation portion 252 from the opening in such a manner that a part of the opening at one end of inhalation portion 252 is open to the outside.

This structure will be described in more detail. A lead-out flow passage 204 extending from the aerosol generation portion to aerosol lead-out opening 205 is constituted with a flow passage portions 204A, 204C provided in introduction portion 251 and a lower part of a flow passage portion 204B provided in inhalation portion 252, and a discharge flow passage extending from aerosol lead-out opening 205 to exhalation discharge opening 206 is constituted with an upper part of flow passage portion 204B provided in inhalation portion 252 and a flow passage portion 204E also provided in inhalation portion 252. Then, a narrow portion 254 is provided at a part of introduction portion 251 such that the cross section of flow passage portion 204C is smaller than the cross section of flow passage portion 204A. In addition, an aerosol outflow opening 255 which is a portion where aerosol flows out from introduction portion 251 to inhalation portion 252 is provided in inhalation portion 252, and an exhalation discharge opening 206 is provided at an end portion of flow passage portion 204E that is a portion positioned in a rear direction from this aerosol outflow opening 255.

Because of such a configuration, as shown in FIG. 21, at the time of inhalation, aerosol passes through the lower side of flow passage portion 204B provided in inhalation portion 251 to reach aerosol lead-out opening 205, and at the time of exhalation discharge, exhalation passes through the upper side of flow passage portion 204B provided in inhalation portion 251 to reach exhalation discharge opening 206, so that prevention of loss of aerosol and elimination of an exhalation valve are realized at the same time.

FIG. 23 is a longitudinal cross-sectional view of an inhaler mouthpiece disclosed in the above-noted Patent Document 2. As shown in FIG. 23, an inhaler mouthpiece 350 disclosed in the above-noted Patent Document 2 includes a lead-out flow passage 304 serving as an ejection flow passage for spray particles which is separated by a partition wall 354 provided inside thereof, and a discharge flow passage serving as a release flow passage for backflow. Lead-out flow passage 304 is formed to extend from an opening at one end that communicates with an aerosol generation portion to aerosol lead-out opening 305 which is an opening at the other end, and the discharge flow passage is formed to extend from aerosol lead-out opening 305 to exhalation discharge opening 306.

This structure will be described in more detail. Lead-out flow passage 304 extending from the aerosol generation portion to aerosol lead-out opening 305 is configured with a first flow passage portion 304A provided in a lower-side tubular portion 351 extending upward from the aerosol generation portion, a lower part of a second flow passage portion 304B provided in an upper-side tubular portion 352 extending obliquely forward to reach aerosol lead-out opening 305, and a corner flow passage portion 304C connecting these first flow passage portion 304A and second flow passage portion 304B with each other, and the discharge flow passage extending from aerosol lead-out opening 305 to exhalation discharge opening 306 is constituted with an upper part of second flow passage portion 304B provided in upper-side tubular portion 352 and a flow passage portion 304E also provided in upper-side tubular portion 352. Then, a narrow portion is formed by partition wall 354 such that the cross section of corner flow passage portion 304C is smaller than the cross section of flow passage portion 304A. In addition, an aerosol outflow opening 355, which is a part where aerosol flows out from this narrow portion to second flow passage portion 304B, is provided in upper-side tubular portion 352, and an exhalation discharge opening 306 is provided in flow passage portion 304E positioned in a rear direction from this aerosol outflow portion 355.

Because of such a configuration, as shown in FIG. 23, at the time of inhalation, aerosol passes through the lower side of second flow passage portion 304B provided in upper-side tubular portion 352 to reach aerosol lead-out opening 305, and at the time of exhalation discharge, exhalation passes through the upper side of second flow passage portion 304B provided in upper-side tubular portion 352 to reach exhalation discharge opening 306, so that prevention of loss of aerosol and elimination of an exhalation valve are realized at the same time.

Patent Document 1: Japanese Utility-Model Laying-Open No. 4-95046

Patent Document 2: Japanese Patent Laying-Open No. 5-337183

DISCLOSURE OF THE INVENTION

Problems to be Solved by the Invention

The structures of inhaler mouthpieces disclosed in the above-noted Patent Documents 1 and 2 are both designed on the precondition that they are used for ultrasonic-type or ultrasonic-mesh-type inhalers. Therefore, if the inhaler mouthpiece having the structure described above is applied to a compressor-type inhaler as it is, it cannot be said the mouthpiece has a suitable shape, and the following problems are likely to arise.

The first problem is leakage of aerosol from an exhalation discharge opening at the time of inhalation. The ejection amount of aerosol in a compressor-type inhaler, that is, the quantity of aerosol flow supplied from the aerosol generation portion into the mouthpiece is as considerably small as a fraction of several to several tens of that of the ultrasonic-type or ultrasonic-mesh-type inhaler. Thus, in the case of usage manner in which the user does not put the mouthpiece into the mouth, part of aerosol flows into the discharge flow passage without being ejected from the aerosol lead-out opening and is left leaking out from the exhalation discharge opening. Accordingly, aerosol is wasted and the inhalation efficiency is considerably reduced.

The second problem is a size increase of the mouthpiece. In the inhaler mouthpieces disclosed in the above-noted Patent Documents 1 and 2, the opening cross section of the aerosol outflow opening is narrowed in order to prevent exhalation introduced into the mouthpiece from intruding into the aerosol generation portion, and the length of the narrow portion is increased to some extent to increase the flow resistance at that part, thereby preventing backflow of exhalation to the aerosol generation portion. Therefore, since it is essential to design a longer narrow portion, the length of the mouthpiece is disadvantageously increased.

If the length of the mouthpiece is increased, aerosol is in contact with the wall surface for a longer time, and therefore spray particles included in the aerosol is liquefied, leading to reduced inhalation efficiency. In particular, when the inhaler mouthpieces disclosed in the above-noted Patent Documents 1 and 2 are applied to compressor-type inhalers, partly because the flow rate of aerosol is slow as compared with a ultrasonic-type or ultrasonic-mesh-type inhaler, aerosol is in contact with the wall surface for a longer time at the aforementioned long narrow portion, and liquefaction of spray particles is noticeable at this narrow portion thereby significantly reducing the inhalation efficiency.

Moreover, in the inhaler mouthpieces disclosed in the above-noted Patent Documents 1 and 2, the lead-out flow passage and the discharge flow passage are stacked one above another by dividing the lead-out flow passage and the discharge-flow passage by a spacer wall. Thus, when the cross sections of the lead-out flow passage and the discharge-flow passage are increased in order to secure the sufficient amount of ejected aerosol and discharged exhalation, the mouthpiece is increased in size upwardly and downwardly. Therefore, the resulting shape is hardly fitted for the mouth.

As described above, there is a strong demand in an inhaler for eliminating an exhalation valve and in addition, an inhalation valve. However, because of the aforementioned problems, in inhalers excluding part of ultrasonic-type and ultrasonic-mesh-type inhalers, actually, exhalation valves and in addition inhalation valves have not yet been eliminated in terms of inhalation efficiency. In part of ultrasonic-type and ultrasonic-mesh-type inhalers from which exhalation valves are eliminated, leakage of aerosol may occur in the usage manner in which the user does not put the mouthpiece into the mouth.

The present invention is therefore made to solve the aforementioned problems and aims to provide an inhaler and an inhaler mouthpiece in which the apparatus is not increased in size even when the conventionally required exhalation valve or in addition an inhalation valve is eliminated, and leakage of aerosol from a pressure regulation opening or an exhalation discharge opening can be prevented efficiently, irrespective of usage manners.

Means for Solving the Problems

An inhaler based on a first aspect of the prevent invention generates aerosol inside an apparatus body and supply the aerosol to outside of the apparatus body to allow a user to inhale the aerosol. The apparatus body includes an aerosol generation portion and an aerosol lead-out portion. The aerosol generation portion includes a reservoir portion storing liquid and an atomization portion atomizing liquid stored in the reservoir portion into spray particles and applying the atomized spray particles to outside air introduced into the apparatus body. The aerosol lead-out portion includes an aerosol lead-out opening leading the generated aerosol to outside of the apparatus body, a lead-out flow passage guiding the generated aerosol from the aerosol generation portion to the aerosol lead-out opening, and an exhalation discharge opening for discharging exhalation of the user introduced from the aerosol lead-out opening to the lead-out flow passage. The lead-out flow passage includes a first flow passage portion extending from the aerosol generation portion in a first direction, a second flow passage portion extending in a second direction that crosses the first direction to reach the aerosol lead-out opening, and a corner flow passage portion joining the first flow passage portion and the second flow passage portion to each other. The aerosol lead-out portion at a part that defines the corner flow passage portion has a curvature portion formed by curving that wall surface which crosses a center line of the first flow passage portion. The exhalation discharge opening is provided on a wall surface at a position that is circumferentially displaced from that wall surface of the aerosol lead-out portion on which the curvature portion is provided and that defines the second flow passage portion. Here, “a wall surface at a position circumferentially displaced from that wall surface on which the curvature portion is provided” means a wall surface, of the wall surface of the lead-out flow passage formed to surround the center axis of the second flow passage portion, that is a part not including that wall surface of the lead-out flow passage on which the curvature portion is provided.

In this manner, the curvature portion is provided at a prescribed position of the aerosol lead-out portion at a part that defines the corner flow passage portion positioned between the first flow passage portion and the second flow passage portion, so that, at a time of inhalation, it becomes possible that aerosol flowing through the first flow passage portion is smoothly guided to the second flow passage portion, and the airflow of aerosol is collected on the wall surface side on which the curvature portion is provided, and is then guided to the second flow passage portion. Therefore, by providing the exhalation discharge opening on the wall surface at a position circumferentially displaced from that wall surface on which the curvature portion is formed, leakage of aerosol from the exhalation discharge opening can effectively be prevented. On the other hand, at a time of exhalation discharge, exhalation is smoothly discharged from the exhalation discharge opening, so that leakage of aerosol from the exhalation discharge opening can be prevented, irrespective of usage manners. Accordingly, the inhalation efficiency can be kept high even without provision of an exhalation valve at the exhalation discharge opening, thereby reducing the number of components to drastically improve the operability in the cleaning and disinfection operations. In addition, the manufacturing costs can significantly be reduced. Furthermore, there is no particular need for providing a narrow portion in the flow passage, and there is no need for providing a discharge flow passage for exhalation discharge, besides the lead-out flow passage for aerosol, thereby possibly reducing the size of the aerosol lead-out portion. Moreover, exhalation flowing into the lead-out flow passage can effectively be discharged from the exhalation discharge opening, so that the necessity to provide an inhalation valve at the pressure regulation opening provided in the aerosol generation portion is reduced, thereby allowing elimination of the inhalation valve.

In the inhaler based on the first aspect of the present invention as described above, preferably, the exhalation discharge opening is provided at a position closer to the corner flow passage portion of the aerosol lead-out portion in a part that defines the second flow passage portion.

The aerosol flowing through the first flow passage portion is collected on that wall surface side on which the curvature portion is provided, in particular, in a part closer to the corner flow passage portion of the second flow passage portion, so that leakage of aerosol from the exhalation discharge opening can reliably be prevented by providing the exhalation discharge opening closer to the corner flow passage portion of the aerosol lead-out portion in a part that defines the second flow passage portion, as described above.

In the inhaler based on the first aspect of the present invention as described above, preferably, the aerosol lead-out portion has a narrow portion, at a position where the exhalation discharge opening is provided, for reducing a cross section of the second flow passage portion toward the aerosol lead-out opening. In this case, preferably, the narrow portion is positioned on an inner side than the exhalation discharge opening in a part of the aerosol lead-out portion where the exhalation discharge opening is provided.

Because of such a configuration, the narrow portion allows the airflow of aerosol to be collected at the radially central position of the second flow passage portion, thereby allowing the airflow of aerosol to be kept away from the exhalation discharge opening and effectively preventing leakage of aerosol from the exhalation discharge opening.

In the inhaler based on the first aspect of the present invention as described above, preferably, the curvature portion has a dome-like shape. In this case, preferably, the narrow portion is formed of a part of the dome-shaped curvature portion.

Because of such a configuration, the curvature portion and the narrow portion are integrally formed in the dome-shaped portion, so that smooth lead-out of aerosol and discharge of exhalation can be realized without complicating the shape of the lead-out flow passage more than necessary.

In the inhaler based on the first aspect of the present invention as described above, preferably, a pair of the exhalation discharge openings is provided in the aerosol lead-out portion at positions between which a plane including a center line of the first flow passage portion and a center line of the second flow passage portion is sandwiched.

Because of such a configuration, a large opening area of the exhalation discharge opening can be secured, thereby ensuring a large amount of exhalation discharge and realizing reliable discharge of exhalation.

An inhaler based on a second aspect of the present invention generates aerosol inside an apparatus body and supply the aerosol to outside of the apparatus body to allow a user to inhale the aerosol. The apparatus body includes an aerosol generation portion and an aerosol lead-out portion. The aerosol generation portion includes a reservoir portion storing liquid and an atomization portion atomizing liquid stored in the reservoir portion into spray particles and applying the atomized spray particles to outside air introduced into the apparatus body. The aerosol lead-out portion includes an aerosol lead-out opening leading the generated aerosol to outside of the apparatus body, a lead-out flow passage guiding the generated aerosol from the aerosol generation portion to the aerosol lead-out opening, and an exhalation discharge opening for discharging exhalation of the user introduced from the aerosol lead-out opening to the lead-out flow passage. The aerosol lead-out portion at a part that defines the lead-out flow passage has a narrow portion, at a position where the exhalation discharge opening is provided, for reducing a cross section of the lead-out flow passage toward the aerosol lead-out opening. The narrow portion is positioned on an inner side than the exhalation discharge opening, in a part of the aerosol lead-out portion where the exhalation discharge opening is provided.

In this manner, the narrow portion is provided in the aerosol lead-out portion at a part where the exhalation discharge opening is provided, so that, at a time of inhalation, the airflow of aerosol can be collected at the radially central position of the second flow passage portion, thereby allowing the airflow of aerosol to be kept away from the exhalation discharge opening and effectively preventing leakage of aerosol from the exhalation discharge opening. On the other hand, at a time of exhalation discharge, exhalation is smoothly discharged from the exhalation discharge opening, so that leakage of aerosol from the exhalation discharge opening can be prevented, irrespective of usage manners. Accordingly, the inhalation efficiency can be kept high even without provision of an exhalation valve at the exhalation discharge opening, thereby reducing the number of components to drastically improve the operability in the cleaning and disinfection operations. In addition, the manufacturing costs can significantly be reduced. Furthermore, there is no particular need for providing a long narrow portion in the flow passage, and there is no need for providing a discharge flow passage for exhalation discharge, besides the lead-out flow passage for aerosol, thereby possibly reducing the size of the aerosol lead-out portion. Moreover, exhalation flowing into the lead-out flow passage can effectively be discharged from the exhalation discharge opening, so that the necessity to provide an inhalation valve at the pressure regulation opening provided in the aerosol generation portion is reduced, thereby allowing elimination of the inhalation valve.

In the inhaler based on the first and second aspects of the present invention as described above, the aerosol generation portion may further include a pressure regulation opening for regulating an internal pressure of the apparatus body. In such a case, preferably, a passage at a part extending from the pressure regulation opening to the atomization portion has its cross section reduced so that flow resistance is higher at a particular part than at other parts of the passage, and includes a labyrinth-like part bent at least once.

In this manner, the shape of the passage extending from the pressure regulation opening to the atomization portion is complicated, so that the flow resistance can be set high at that part, thereby more reliably preventing leakage of aerosol from the pressure regulation opening. Therefore, leakage of aerosol due to elimination of an inhalation valve can be prevented more reliably.

In the inhaler based on the first and second aspects of the present invention as described above, preferably, the aerosol lead-out portion is removably attached to the aerosol generation portion.

Because of such a configuration, the handling ease in the cleaning and disinfection operations is improved, resulting in a hygienically excellent inhaler.

An inhaler mouthpiece based on a first aspect of the present invention is removably attached to an aerosol generation portion of an inhaler for leading aerosol generated in the aerosol generation portion to outside of the aerosol generation portion, and includes: an aerosol lead-out opening leading aerosol generated in the aerosol generation portion to outside; a lead-out flow passage guiding the generated aerosol from the aerosol generation portion to the aerosol lead-out opening; and an exhalation discharge opening for discharging exhalation of a user introduced from the aerosol lead-out opening to the lead-out flow passage. The lead-out flow passage includes a first flow passage portion extending from the aerosol generation portion in a first direction, a second flow passage portion extending in a second direction that crosses the first direction to reach the aerosol lead-out opening, and a corner flow passage portion joining the first flow passage portion and the second flow passage portion to each other. A curvature portion is provided at a part that defines the corner flow passage portion by curving that wall surface which crosses a center line of the first flow passage portion. The exhalation discharge opening is provided on a wall surface at a position circumferentially displaced from that wall surface on which the curvature portion is provided and that defines the second flow passage portion. Here, "a wall surface at a position circumferentially displaced from that wall surface on which the curvature portion is provided" means a wall surface, of the wall surface of the lead-out flow passage formed to surround the center axis of the second flow passage portion, that is a part not including that wall surface of the lead-out flow passage on which the curvature portion is provided.

In this manner, the curvature portion is provided at a prescribed position of a part that defines the corner flow passage portion positioned between the first flow passage portion and the second flow passage portion, so that, at a time of inhalation, it becomes possible that aerosol flowing through the first flow passage portion is smoothly guided to the second flow passage portion, and the airflow of aerosol is collected on that wall surface side on which the curvature portion is provided, and is then guided to the second flow passage portion. Therefore, by providing the exhalation discharge opening on the wall surface at a position circumferentially displaced from that wall surface on which the curvature portion is formed, leakage of aerosol from the exhalation discharge opening can effectively be prevented. On the other hand, at a time of exhalation discharge, exhalation is smoothly discharged from the exhalation discharge opening, so that leakage of aerosol from the exhalation discharge opening can be prevented, irrespective of usage manners. Accordingly, the inhalation efficiency can be kept high even without provision of an exhalation valve at the exhalation discharge opening, thereby reducing the number of components to drastically improve the operability in the cleaning and disinfection operations. In addition, the manufacturing costs can significantly be reduced. Furthermore, there is no particular need for providing a narrow portion in the flow passage, and there is no need for providing a discharge flow passage for exhalation discharge, besides the lead-out flow passage for aerosol, thereby possibly reducing the size of the inhaler mouthpiece.

In the inhaler mouthpiece based on the first aspect of the present invention as described above, preferably, the exhalation discharge opening is provided at a position closer to the corner flow passage portion in a part that defines the second flow passage portion.

The aerosol flowing through the first flow passage portion is collected on that wall surface side on which the curvature portion is provided, in particular, in a part closer to the corner flow passage portion of the second flow passage portion, so that leakage of aerosol from the exhalation discharge opening can reliably be prevented by providing the exhalation discharge opening closer to the corner flow passage portion in a part that defines the second flow passage portion, as described above.

In the inhaler mouthpiece based on the first aspect of the present invention as described above, preferably, a narrow portion is provided at a position where the exhalation discharge opening is provided, for reducing a cross section of the second flow passage portion toward the aerosol lead-out opening. In this case, the narrow portion is positioned on an inner side than the exhalation discharge opening, in a part where the exhalation discharge opening is provided.

Because of such a configuration, the narrow portion allows the airflow of aerosol to be collected at the radially central position of the second flow passage portion, thereby allowing the airflow of aerosol to be kept away from the exhalation discharge opening and effectively preventing leakage of aerosol from the exhalation discharge opening.

In the inhaler mouthpiece based on the first aspect of the present invention as described above, preferably, the curvature portion has a dome-like shape. In this case, preferably, the narrow portion is formed of a part of dome-shaped curvature portion.

Because of such a configuration, the curvature portion and the narrow portion are integrally formed in the dome-shaped portion, so that smooth lead-out of aerosol and discharge of exhalation can be realized without complicating the shape of the lead-out flow passage more than necessary.

In the inhaler mouthpiece based on the first aspect of the present invention as described above, preferably, a pair of the exhalation discharge openings is provided at positions between which a plane including a center line of the first flow passage portion and a center line of the second flow passage portion is sandwiched.

Because of such a configuration, a large opening area of the exhalation discharge opening can be secured, thereby ensuring a large amount of exhalation discharge and realizing reliable discharge of exhalation.

An inhaler mouthpiece based on a second aspect of the present invention is removably attached to an aerosol generation portion of an inhaler for leading aerosol generated inside the aerosol generation portion to outside of the aerosol generation portion, and includes: an aerosol lead-out opening leading aerosol generated in the aerosol generation portion to outside; a lead-out flow passage guiding the generated aerosol from the aerosol generation portion to the aerosol lead-out opening; and an exhalation discharge opening for discharging exhalation of a user introduced from the aerosol lead-out opening to the lead-out flow passage. Then, a narrow portion is provided at a position where the exhalation discharge opening is provided, for reducing a cross section of the lead-out flow passage toward the aerosol lead-out opening. The narrow portion is positioned on an inner side than the exhalation discharge opening, in a part where the exhalation discharge opening is provided.

In this manner, the narrow portion is provided at a part where the exhalation discharge opening is provided, so that, at a time of inhalation, the airflow of aerosol can be collected at the radially central position of the second flow passage portion, thereby allowing the airflow of aerosol to be kept away from the exhalation discharge opening and effectively preventing leakage of aerosol from the exhalation discharge opening. On the other hand, at a time of exhalation discharge, exhalation is smoothly discharged from the exhalation discharge opening, so that leakage of aerosol from the exhalation discharge opening can be prevented, irrespective of usage manners. Accordingly, the inhalation efficiency can be kept high even without provision of an exhalation valve at the exhalation discharge opening, thereby reducing the number of components to drastically improve the operability in the cleaning and disinfection operations. In addition, the manufacturing costs can significantly be reduced. Furthermore, there is no particular need for providing a long narrow portion in the flow passage, and there is no need for providing a discharge flow passage for exhalation discharge, besides the lead-out flow passage for aerosol, thereby possibly reducing the size of the aerosol lead-out portion. Moreover, exhalation flowing into the lead-out flow passage can effectively be discharged from the exhalation discharge opening, so that the necessity to provide an inhalation valve at the pressure regulation opening provided in the aerosol generation portion is reduced, thereby allowing elimination of the inhalation valve.

Effects of the Invention

In accordance with the present invention, it is possible to eliminate an exhalation valve or in addition an inhalation valve in an inhaler, and it is possible to eliminate an exhalation valve in an inhaler mouthpiece. Even in such a case, leakage of aerosol from a pressure regulation opening or an exhalation discharge opening can effectively be prevented without increasing the size of the inhaler and the inhaler mouthpiece and irrespective of usage manners.

BRIEF DESCRIPTION OF THE DRAWINGS

FIG. 4 is a cross-sectional view of the nebulizer of the inhaler in the first embodiment of the present invention.

FIG. 18 is a cross-sectional view of the inhaler mouthpiece in the third embodiment of the present invention.

FIG. 19 is an illustration showing an airflow at a time of inhalation in the inhaler mouthpiece in the third embodiment of the present invention.

FIG. 20 is an illustration showing an airflow at a time of exhalation discharge in the inhaler mouthpiece in the third embodiment of the present invention.

FIG. 21 is a longitudinal cross-sectional view of an exemplary configuration of a conventional inhaler mouthpiece.

FIG. 22 is a front view of the inhaler mouthpiece shown in FIG. 21.

FIG. 23 is a longitudinal cross-sectional view of another exemplary configuration of a conventional inhaler mouthpiece.

DESCRIPTION OF THE REFERENCE SIGNS 1 inhaler, 10 compressor, 20 tube, 30 liquid, 100 nebulizer, 101 pressure regulation opening, 102 introduction flow passage, 103 aerosol transfer flow passage, 104 lead-out flow passage, 104A first flow passage portion, 104B second flow passage portion, 104C corner flow passage portion, 105 aerosol lead-out opening, 106 exhalation discharge opening, 110 case body, 114 compressed air introduction pipe portion, 116 reservoir portion, 118 mark, 119 engagement concave portion, 120 atomization portion forming body, 122 baffle, 124 inhaled liquid pipe forming portion, 130 flow passage forming body, 132 connection portion, 133 opening portion, 134 inhalation pipe portion, 138 mark, 139 engagement convex portion, 140 cap body, 141 outer circumferential surface, 142 concave portion, 150A-150C mouthpiece, 151 lower-side tubular portion, 152 upper-side tubular portion, 153 curvature portion, 154 narrow portion, 155 aerosol outflow opening.

Best Modes for Carrying out the Invention

In the following, embodiments of the present invention will be described in detail with reference to the figures. It is noted that in the embodiments illustrated below, a compressor-type inhaler will be described as an illustrative example of an inhaler.

(First Embodiment)

Figure 1:
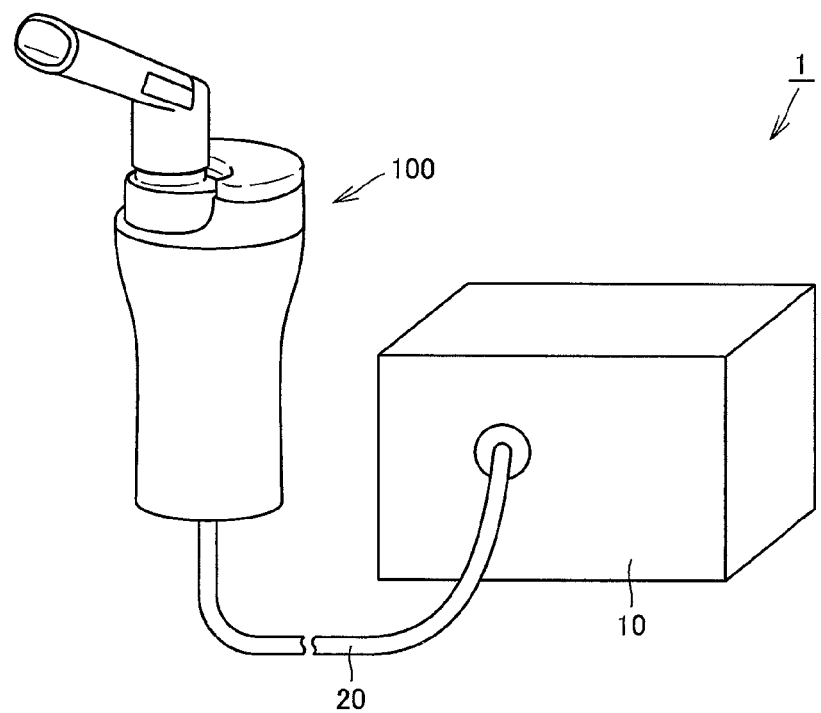
FIG. 1 is an external view showing an apparatus configuration of an inhaler in a first embodiment of the present invention.

FIG. 1 is an external view showing an apparatus configuration of an inhaler in a first embodiment of the present invention. As shown in FIG. 1, an inhaler 1 in this embodiment includes a compressor 10, a tube 20, and a nebulizer 100 as an apparatus body. Compressor 10 is connected to nebulizer 100 through tube 20 having flexibility, and compressed air is sent to nebulizer 100 through this tube 20.

Figure 2A:
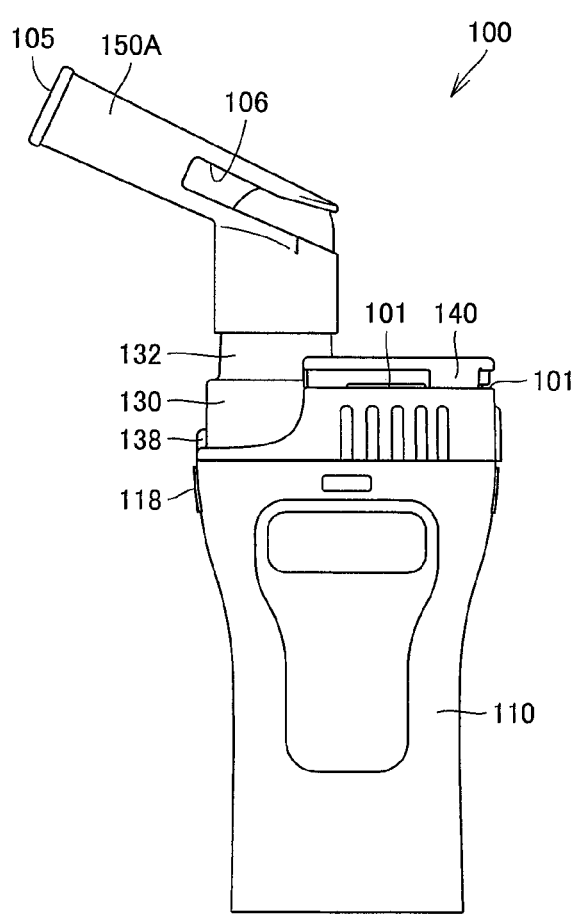
FIG. 2A is a side view showing a structure of a nebulizer of the inhaler in the first embodiment of the present invention.
Figure 2B:
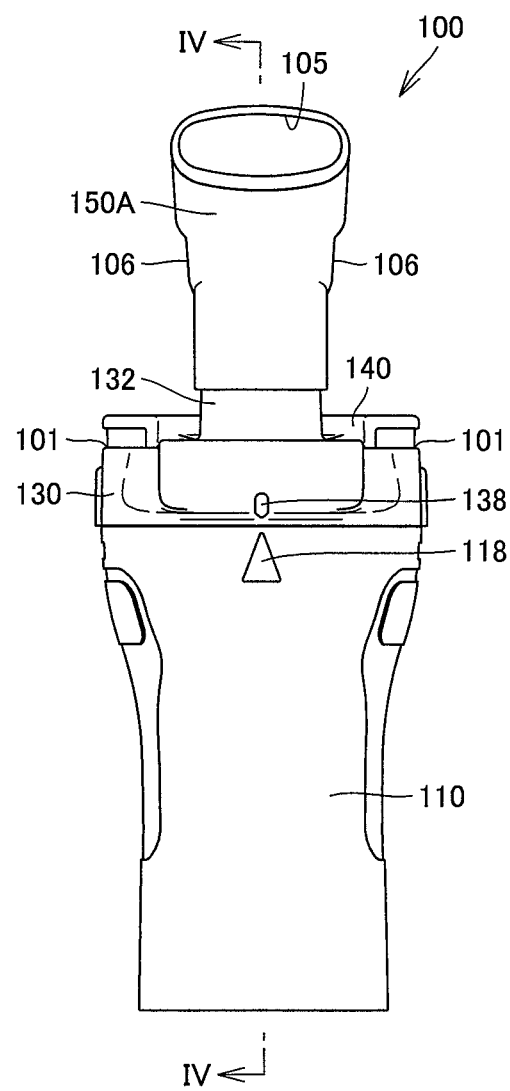
FIG. 2B is a front view showing the structure of the nebulizer of the inhaler in the first embodiment of the present invention.
Figure 3:
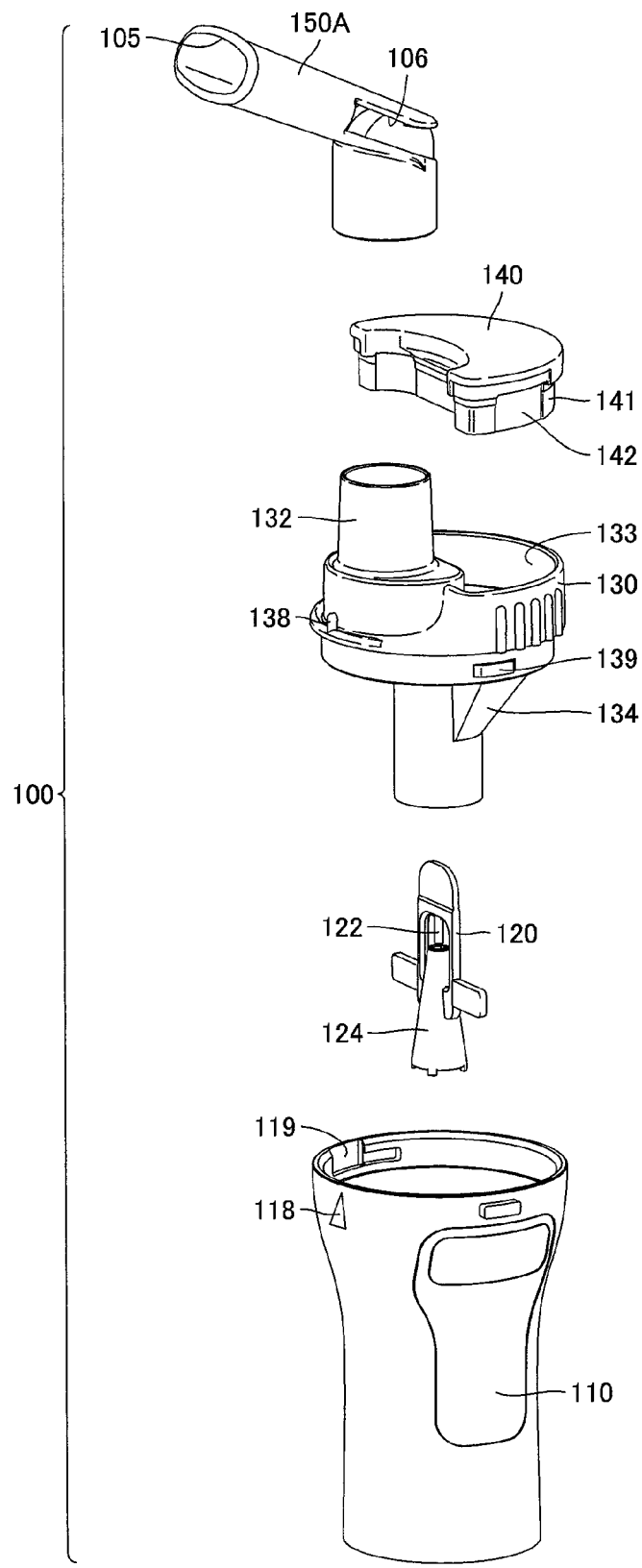
FIG. 3 is an exploded perspective view showing a construction structure of the nebulizer in the first embodiment of the present invention.

FIG. 2A and FIG. 2B are views showing the detailed structure of the nebulizer of the inhaler shown in FIG. 1, where FIG. 2A is a side view and FIG. 2B is a front view. FIG. 3 is an exploded perspective view showing a construction structure of the nebulizer shown in FIG. 2A and FIG. 2B. As shown in FIG. 2A, FIG. 2B and FIG. 3, nebulizer 100 includes a case body 110, an atomization portion forming body 120, a flow passage forming body 130, a cap body 140, and a mouthpiece 150A. Among these, case body 110, atomization portion forming body 120, flow passage forming body 130, and cap body 140 constitute an aerosol generation portion which generates aerosol by atomizing liquid into spray-like particles and applying the spray particles to the introduced outside air. Mouthpiece 150A forms an aerosol lead-out portion which ejects the generated aerosol to the oral cavity or nasal cavity of the user.

Case body 110 has a cylindrical shape with a bottom part, and atomization portion forming body 120 is accommodated and arranged inside this case body 110. Flow passage forming body 130 is attached on the top of case body 110 to close the top-face opening of case body 110. Cap body 140 is attached to flow passage forming body 130 to cover an opening provided on the top face of flow passage forming body 130. Mouthpiece 150A is removably attached to a connection portion 132 provided on the top of flow passage forming body 130. It is noted that case body 110, atomization portion forming body 120, flow passage forming body 130, cap body 140, and mouthpiece 150A can be disassembled and assembled from/to each other to facilitate cleaning, disinfection and the like after the use of inhaler 1.

As shown in FIG. 3, at a prescribed position of the upper part of the inner circumferential surface of case body 110, an engagement concave portion 119 is formed by providing a groove, and at a prescribed position of the lower part of the outer circumferential surface of flow passage forming body 130, an engagement convex portion 139 is formed by providing a projection. These engagement concave portion 119 and engagement convex portion 139 form an engagement portion in attaching flow passage forming body 130 to case body 110.

As shown in FIG. 2A, FIG. 2B and FIG. 3, a mark 118 is provided at a prescribed position of the upper part of the outer circumferential surface of case body 110, and a mark 138 is provided at a prescribed position of the lower part of the outer circumferential surface of flow passage forming body 130. These marks 118, 138 are indicators showing an attachment position of flow passage forming body 130 to case body 110, so that flow passage forming portion 130 is attached to case body 110 such that mark 118 and mark 138 face each other, in assembly.

As shown in FIG. 3, atomization portion forming body 120 includes a baffle 122 and an inhaled liquid pipe forming portion 124. Baffle 122 has a cylindrical shape, and inhaled liquid pipe forming portion 124 is formed of a conical tubular body having an opening at a tip end thereof. Inhaled liquid pipe forming portion 124 has its tip end facing the lower end of baffle 122.

Flow passage forming body 130 includes a connection portion 132, an opening portion 133, and an inhalation pipe portion 134. Connection portion 132 is a part to which mouthpiece 150A is connected, as described above, and is projected upward at a prescribed position of the upper part of flow passage forming body 130. Opening portion 133 is a part in which the lower part of cap body 140 is fitted, and is provided at a prescribed position of the top face of flow passage forming body 130. Inhalation pipe portion 134 is a part for guiding the outside air introduced from a pressure regulation opening 101 (see FIG. 2A and FIG. 2B) as described later into an atomization portion as described later and is projected downward at a prescribed position of the lower part of flow passage forming body 130.

At a prescribed position of an outer circumferential surface 141 of cap body 140, a concave portion 142 is provided. The lower part of this concave portion 142 is arranged to face the inner circumferential surface of flow passage forming body 130 in a state where cap body 140 is attached to flow passage forming body 130, whereby a gap between outer circumferential surface 141 of cap body 140 and the inner circumferential surface of flow passage forming body 130 forms pressure regulation opening 101.

As shown in FIG. 2A, FIG. 2B and FIG. 3, mouthpiece 150A is formed of a tubular member bent at an approximately middle portion thereof, and a lead-out flow passage 104 (see FIG. 4) as described later is provided inside. At the tip end of mouthpiece 150A, an aerosol lead-out opening 105 is provided for ejecting aerosol. In addition, at prescribed positions of the opposite side surfaces of mouthpiece 150A, a pair of exhalation discharge openings 106 is provided for discharging exhalation. It is noted that the detailed shape of mouthpiece 150A will be described later.

FIG. 4 is a cross-sectional view taken along line IV-IV shown in FIG. 2B, of the nebulizer of the inhaler in the present embodiment. In the following, referring to FIG. 4, an internal structure of nebulizer 100 in the present embodiment and an airflow formed therein will be described in detail.

As shown in FIG. 4, at the bottom face of case body 110, a compressed air introduction pipe portion 114 is disposed to extend upward and downward for introducing compressed air sent from compressor 10 to the inside of case body 110. The aforementioned tube 20 is attached to the lower tip end portion of compressed air introduction pipe portion 114. The upper tip end portion of compressed air introduction pipe portion 114 is formed in a tapered shape and faces baffle 122 of atomization portion forming body 120. In addition, around the portion of case body 110 in which compressed air introduction pipe portion 114 is formed, a reservoir portion 116 is provided. This reservoir portion 116 temporarily stores liquid 30 such as water, saline solution or chemical solution.

At the upper tip end portion of compressed air introduction pipe portion 114, inhaled liquid pipe forming portion 124 of atomization portion forming body 120 is arranged from above to face thereto. The inner circumferential surface of this inhaled liquid pipe forming portion 124 is arranged to be positioned at a prescribed distance from the outer circumferential surface of compressed air introduction pipe portion 114 and the lower end thereof reaches the vicinity of the bottom surface of the aforementioned reservoir portion 116. The gap between inhaled liquid pipe forming portion 124 and compressed air introduction pipe portion 114 forms an inhaled liquid pipe, and the action of negative pressure produced by blowing compressed air as described later causes liquid 30 stored in reservoir portion 116 to reach the vicinity of the atomization portion as described later.

The atomization portion is formed between the upper tip end portion of compressed air introduction pipe portion 114 as described above and baffle 122. In this atomization portion, compressed air introduced to compressed air introduction pipe portion 114 by compressor 10 is sprayed toward baffle 122 from the upper tip end portion of compressed air introduction pipe portion 114. At that time, liquid 30 sucked up to the vicinity of the atomization portion by the action of negative pressure produced in the atomization portion blows up to the atomization portion by the action of the aforementioned negative pressure and is sprayed toward baffle 122 together with compressed air. By means of this action, liquid 30 impinges on baffle 122 to become fine droplets and then spray particles, and the spray particles are applied to the outside air (including the outside air introduced by compressor 10 and the outside air introduced from pressure regulation opening 101 based on the user's exhalation operation) introduced into case body 110 to generate aerosol.

Above atomization portion forming body 120, flow passage forming body 130 is positioned and arranged. This flow passage forming body 130 partitions the space inside case body 110 to form a flow passage in which airflow flows. More specifically, the space inside case body 110 is partitioned into a central portion and a peripheral portion by an inhalation pipe portion 134 provided to the lower part of flow passage forming body 130, and the central portion forms an introduction flow passage 102 and the peripheral portion forms an aerosol transfer flow passage 103. Introduction flow passage 102 is a flow passage for guiding, to the atomization portion, the outside air flowing in from pressure regulation opening 101 formed by the gap between cap body 140 fitted in an opening portion 133 provided at the top face of flow passage forming portion 130 and flow passage forming portion 130. Aerosol transfer flow passage 103 is a flow passage for guiding aerosol generated in the atomization portion to mouthpiece 150A.

In nebulizer 100 of inhaler 1 in the present embodiment, inhalation pipe portion 134 is disposed to cover the side of the atomization portion. Because of such a configuration, of spray particles generated by impingement on baffle 122, spray particles having a relatively large particle size come into contact with the inner circumferential surface of inhalation pipe portion 134 to liquefy and return to reservoir portion 116 on the inner circumferential surface of inhalation pipe portion 134. On the other hand, spray particles having a relatively small particle size flow into aerosol transfer flow passage 103 without liquefying. Therefore, only spray particles with a fine particle size suitable for inhalation can be selectively guided to mouthpiece 150A. In particular, when chemical solution is atomized and inhaled, it is important to form aerosol including spray particles with a particle size suitable for treatment, and employment of the configuration as described above is meaningful.

As described above, mouthpiece 150A is attached to connection portion 132 provided on the top face of flow passage forming body 130, so that aerosol transfer flow passage 103 provided inside case body 110 and lead-out flow passage 104 provided inside mouthpiece 150A communicate with each other.

In inhaler 1 configured as described above, the airflow is as follows, in a case where the user puts mouthpiece 150A into the mouth to inhale aerosol. When inhaler 1 is operated, the outside air is introduced into case body 110 by compressor 10 so that aerosol is always generated in the atomization portion. At a time of inhalation, the user performs an inhalation operation to take in aerosol whereby a negative pressure is developed in the internal space of case body 110 through lead-out flow passage 104 of mouthpiece 150A. Accordingly, the outside air is taken into the inside of case body 110 from pressure regulation opening 101. The taken-in outside air passes through introduction flow passage 102 formed inside inhalation pipe portion 134 to the atomization portion. Then, spray particles are applied in the atomization portion to the outside air including the outside air introduced by the aforementioned compressor 10 and the outside air introduced from pressure regulation opening 101 based on the exhalation operation of the user, thereby generating aerosol. The generated aerosol passes through aerosol transfer flow passage 103 to flow into lead-out flow passage 104 of mouthpiece 150A. The aerosol flowing into lead-out flow passage 104 is ejected toward the oral cavity of the user from aerosol lead-out opening 105 based on the inhalation operation of the user. It is noted that inhaler 1 in the present embodiment is characterized by the shape of mouthpiece 150A as described later, which effectively prevents leakage of aerosol from exhalation discharge opening 106 of mouthpiece 150A to the outside at a time of inhalation.

At a time of exhalation discharge, the user exhales the breath so that the exhalation is introduced into lead-out flow passage 104 of mouthpiece 150A. The exhalation introduced into lead-out flow passage 104 is discharged from exhalation discharge opening 106 provided at mouthpiece 150A to the outside. Here, inhaler 1 in the present embodiment is characterized by the shape of mouthpiece 150A as described later, so that almost all the exhalation introduced into lead-out flow passage 104 is effectively discharged from exhalation discharge opening 106 to the outside. Therefore, backflow of exhalation toward aerosol transfer flow passage 103, that is, to the inside of case body 110 can be prevented.

In addition, in inhaler 1 configured as described above, the airflow in a case where the user confronts mouthpiece 150A to inhale aerosol ejected from mouthpiece 150A without putting mouthpiece 150A into the mouth is approximately similar to the airflow at a time of inhalation in a case where the above-mentioned user puts mouthpiece 150A into the mouth for inhalation. However, since a negative pressure is not developed inside case body 110 by the inhalation operation of the user, only the compressed air sent from compressor 10 contributes to taking-in of outside air or lead-out of aerosol, and the action of compressor 10 allows aerosol to be continuously ejected from aerosol lead-out opening 105. Inhaler 1 in the present embodiment is characterized by the shape of mouthpiece 150A as described later, so that leakage of aerosol from exhalation discharge opening 106 of mouthpiece 150A to the outside can also effectively be prevented in the usage manner as described above.

Figure 5:
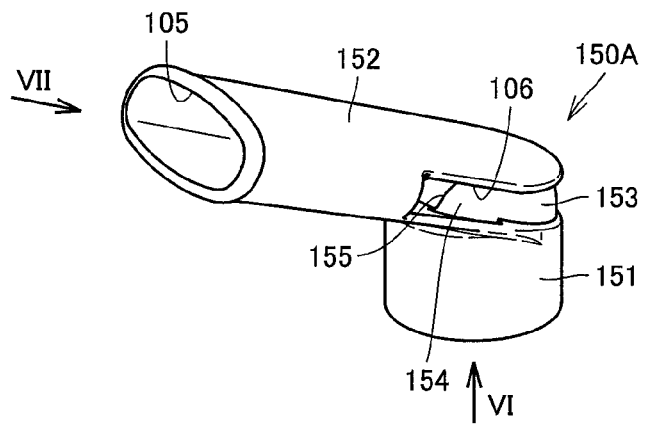
FIG. 5 is a perspective view of an inhaler mouthpiece in the first embodiment of the present invention.
Figure 6:
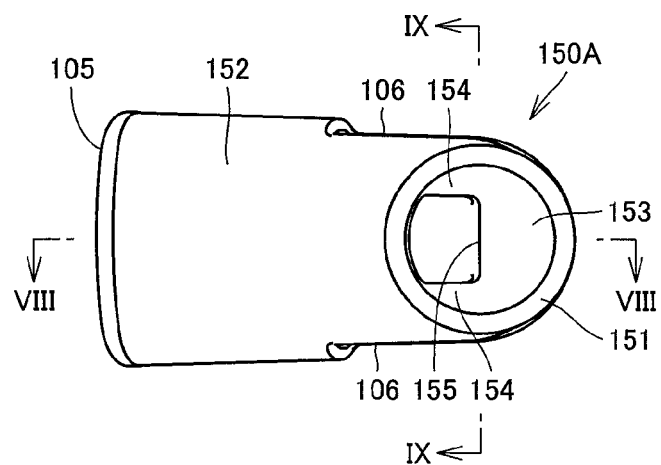
FIG. 6 is a bottom view of the inhaler mouthpiece in the first embodiment of the present invention.
Figure 7:
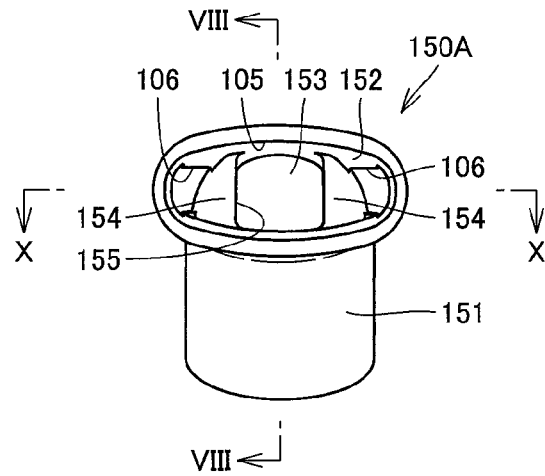
FIG. 7 is a perspective view of the inhaler mouthpiece in the first embodiment of the present invention.
Figure 8:
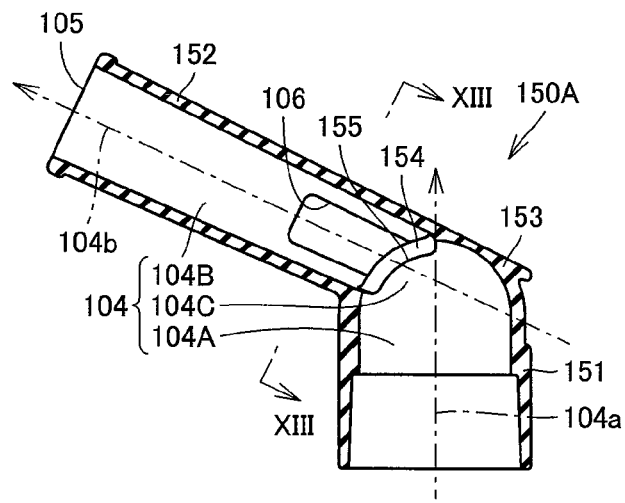
FIG. 8 is a cross-sectional view of the inhaler mouthpiece in the first embodiment of the present invention.
Figure 9:
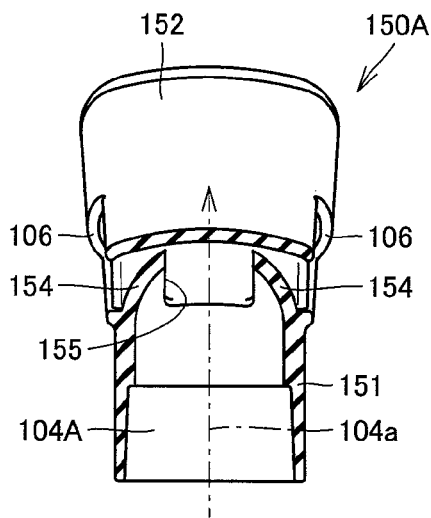
FIG. 9 is a cross-sectional view of the inhaler mouthpiece in the first embodiment of the present invention.
Figure 10:
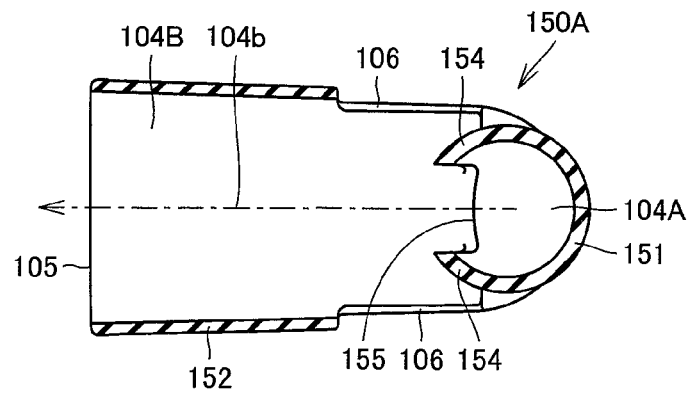
FIG. 10 is a cross-sectional view of the inhaler mouthpiece in the first embodiment of the present invention.

FIG. 5 to FIG. 10 are views showing the shape of the inhaler mouthpiece in the present embodiment. Among these, FIG. 5 is a perspective view of the inhaler mouthpiece, FIG. 6 is a bottom view as viewed from arrow VI shown in FIG. 5, and FIG. 7 is a perspective view as viewed from arrow VII shown in FIG. 5. FIG. 8 is a cross-sectional view taken along line VIII-VIII shown in FIG. 6 and FIG. 7, and FIG. 9 is a cross-sectional view taken along line IX-IX show in FIG. 6. FIG. 10 is a cross-sectional view taken along line X-X shown in FIG. 7. In the following, the shape of inhaler mouthpiece 150A in the present embodiment will be described with reference to these figures.

As shown in FIG. 5 to FIG. 10, inhaler mouthpiece 150A in the present embodiment is connected to connection portion 132 of flow passage forming body 130 and is formed of a tubular member having a lower-side tubular portion 151 extending upward and an upper-side tubular portion 152 extending obliquely forward from lower-side tubular portion 151. Inside lower-side tubular portion 151, a first flow passage portion 104A is formed extending upward (in a first direction 104a). Inside upper-side tubular portion 152, a second flow passage portion 104B is formed extending obliquely upward (in a second direction 104b). In addition, on the inside of a portion connecting lower-side tubular portion 151 to upper-side tubular portion 152, a corner flow passage portion 104C is formed connecting first flow passage portion 104A and second flow passage portion 104B to each other. First flow passage portion 104A, second flow passage portion 104B and corner flow passage portion 104C constitute lead-out flow passage 104 for leading out aerosol. It is noted that at the lower end of lower-side tubular portion 151, an opening is positioned to bring the aforementioned aerosol transfer flow passage 103 and first flow passage portion 104A into communication with each other. On the other hand, at the tip end of upper-side tubular portion 152, aerosol lead-out opening 105 is positioned for leading aerosol to the outside.

At a wall defining corner flow passage portion 104C on that side which crosses the center line of first flow passage portion 104A of mouthpiece 150A, a curvature portion 153 is positioned which is formed by forming such a curve that smoothly joins a wall defining first flow passage portion 104A and a wall defining second flow passage portion 104B to each other. This curvature portion 153 has a dome-like shape and is partially notched at a portion which faces aerosol lead-out opening 105, thereby forming aerosol outflow opening 155.

A part of curvature portion 153 having a dome-like shape that defines aerosol outflow opening 155 forms a narrow portion 154 which reduces the cross section of second flow passage portion 104B toward aerosol lead-out opening 105. On the opposite surfaces of upper-side tubular portion 152 at positions corresponding to a part where narrow portion 154 is provided, a pair of exhalation discharge openings 106 is respectively provided. Therefore, narrow portion 154 is positioned on the inner side than exhalation discharge openings 106 at a part of second flow passage portion 104B in which exhalation discharge openings 106 are provided.

Figure 11A:
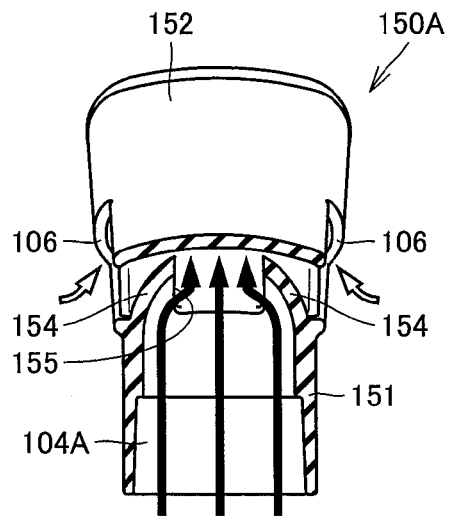
FIG. 11A is an illustration showing an airflow at a time of inhalation in the inhaler mouthpiece in the first embodiment of the present invention.
Figure 11B:
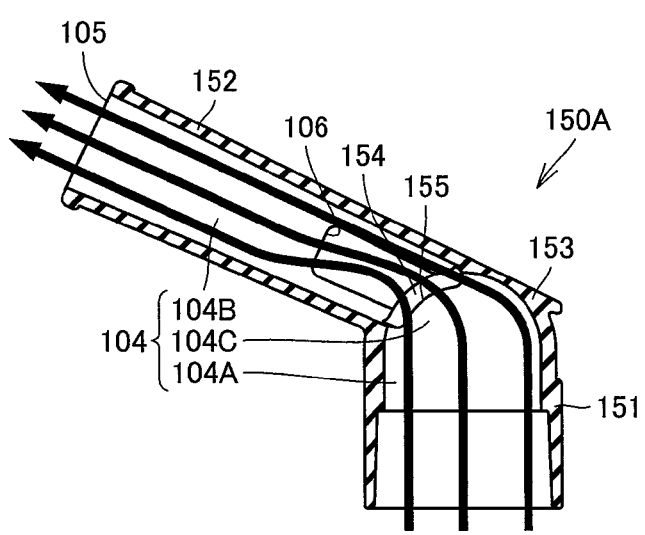
FIG. 11B is an illustration showing an airflow at a time of inhalation in the inhaler mouthpiece in the first embodiment of the present invention.
Figure 11C:
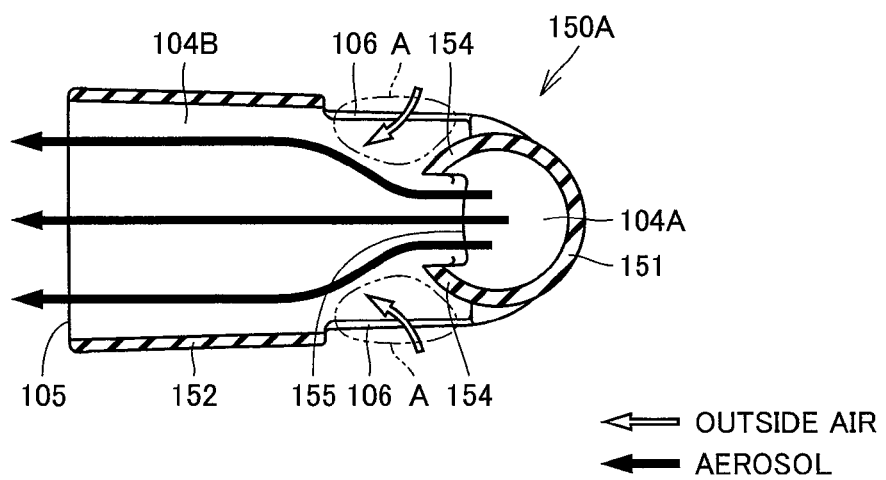
FIG. 11C is an illustration showing an airflow at a time of inhalation in the inhaler mouthpiece in the first embodiment of the present invention.
Figure 12:
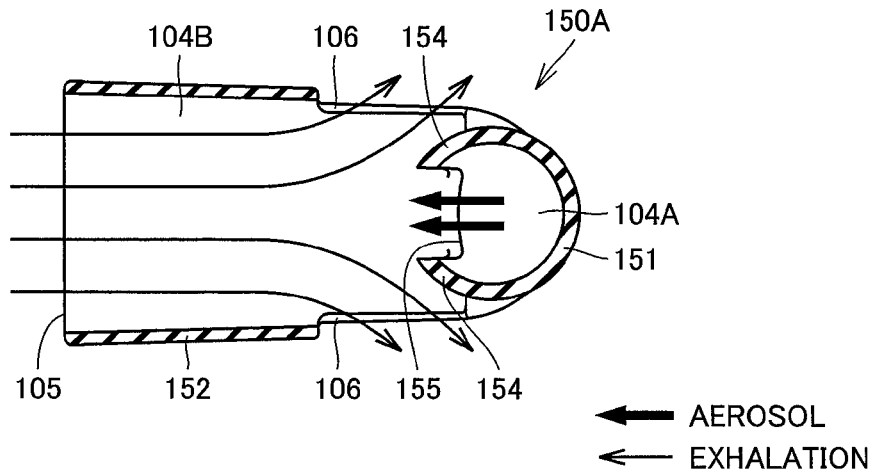
FIG. 12 is an illustration showing an airflow at a time of exhalation discharge in the inhaler mouthpiece in the first embodiment of the present invention.

FIG. 11A to FIG. 11C are illustrations showing the airflow at a time of inhalation in the inhaler mouthpiece in the present embodiment. FIG. 12 is an illustration showing the airflow at a time of exhalation discharge in the inhaler mouthpiece in the present embodiment. Here, FIG. 11A to FIG. 11C respectively show the airflows in cross section, respectively corresponding to FIG. 9, FIG. 8. FIG. 10 as described above, and FIG. 12 shows the airflow in cross section corresponding to FIG. 10 as described above. It is noted that any of FIG. 11A to FIG. 11C and FIG. 12 are intended for the case where the user puts the mouthpiece into the mouth for inhalation. However, the airflow in the case where the user confronts the mouthpiece to take in the aerosol ejected from the mouthpiece without putting the mouthpiece into the mouth is also similar to that of FIG. 11A to FIG. 11C as described above, and therefore illustration thereof will not be repeated here. In the following, with reference to these figures, the airflow in the inhaler mouthpiece in the present embodiment will be described.

In mouthpiece 150A configured as described above, the airflow in the case where the user puts mouthpiece 150A into the mouth for inhalation is as follows. As shown in FIG. 11A and FIG. 11B, aerosol flowing from aerosol transfer flow passage 103 into first flow passage portion 104A of mouthpiece 150A flows upward and reaches corner flow passage portion 104C. The aerosol reaching corner flow passage portion 104C flows along dome-like curvature portion 153 and passes through aerosol outflow opening 155 to reach second flow passage portion 104B.

Here, aerosol is smoothly introduced from first flow passage portion 104A to second flow passage portion 104B in the presence of curvature portion 153 so that the flow of aerosol is not disturbed in corner flow passage portion 104C. Furthermore, aerosol is narrowed down by narrow portion 154 which is a part of dome-like curvature portion 153 and is collected at the radially central position of second flow passage portion 104B, as shown in FIG. 11A and FIG. 11C, and in addition, is collected at that wall surface of second flow passage portion 104B on which curvature portion 153 is formed, as shown in FIG. 11B. Therefore, at the part positions where exhalation discharge openings 106 are provided, aerosol passes through the position further away from exhalation discharge openings 106, and in addition, a negative pressure is produced in the vicinity of the part where exhalation discharge openings 106 are provided (the part shown by region A in FIG. 11C), so that the outside air is introduced from exhalation discharge openings 106 and therefore aerosol is not likely to leak from exhalation discharge openings, thereby reliably preventing waste of aerosol. In summary, the pair of exhalation discharge openings 106 are provided, as shown in these Figures, on the side walls of the tubular portion 152 that directly defines the second flow passage portion 104B at positions that are circumferentially displaced from the wall surface portion at which the curvature portion 153 is provided, there being nothing between the pair of exhalation discharge openings 106 to block the flow inside the second flow passage portion 104B because the side walls of the second flow passage portion on which these exhalation discharge openings 106 are provided themselves directly defines the passage.

The aerosol flowing into second flow passage portion 104B spreads out in a fan-like form, as shown in FIG. 11C and thereafter is led out into the oral cavity of the user from aerosol lead-out opening 105. In mouthpiece 150A in the present embodiment, since exhalation discharge openings 106 are provided at positions closer to corner flow passage portion 104C of mouthpiece 150A which defines second flow passage portion 104B, aerosol passes through the part where exhalation discharge openings 106 are provided, before spreading out in a fan-like form, thereby reliably preventing leakage of aerosol.

On the other hand, at a time of exhalation discharge, exhalation introduced to second flow passage portion 104B of mouthpiece 150A by the user exhaling the breath is discharged from exhalation discharge openings 106 provided in second flow passage portion 104B to the outside, as shown in FIG. 12. Here, aerosol tends to flow in second flow passage portion 104B from aerosol outflow opening 155 because of the feeding pressure of compressor 10, but there is no fear that aerosol leaks out from exhalation discharge openings 106 since the flowing pressure of exhalation is usually larger.

In addition, since a large part of exhalation is discharged from exhalation discharge openings 106 without flowing into first flow passage portion 104A through aerosol outflow opening 155, no exhalation flows into the interior space of case body 110 and thus no aerosol leaks out from pressure regulation opening 101. In particular, in inhaler 1 in the present embodiment, at the part where pressure regulation opening 101 is formed (that is, the gap portion between the outer circumferential surface of cap body 140 and the inner circumferential surface of flow passage forming body 130), the cross section of introduction flow passage 102 for outside air is reduced as compared with the other parts and, in addition, the flow passage is bent, so that introduction flow passage 102 for the outside air is complicated at this part to increase the flow resistance, thereby reliably preventing leakage of aerosol from pressure regulation opening 101.

Furthermore, in inhaler 1 configured as described above, the airflow in the case where the user confronts mouthpiece 150A to inhale aerosol ejected from mouthpiece 150A without putting mouthpiece 150A into the mouth is also approximately similar to the airflow at the time of inhalation in the case where the aforementioned user puts mouthpiece 150A into the mouth for inhalation. However, since a negative pressure is not developed inside case body 110 by the inhalation operation of the user, only compressed air sent from compressor 10 contributes to taking-in of the outside air and lead-out of aerosol, and aerosol is continuously ejected from aerosol lead-out opening 105 by the action of compressor 10. It is noted that in mouthpiece 150A in the present embodiment, here, leakage of aerosol is also effectively prevented, which mechanism is the same as that at a time of inhalation in the case where the aforementioned user puts mouthpiece 150A into the mouth for inhalation.

As described above, inhaler 1 and inhaler mouthpiece 150A as in the present embodiment can prevent aerosol from leaking out from exhalation discharge openings 106, irrespective of usage manners. Therefore, even without provision of an exhalation valve at exhalation discharge opening 106, the inhalation efficiency can be kept high, thereby reducing the number of components to drastically improve the operability at the time of cleaning and disinfection operations. In addition, the manufacturing costs can be reduced significantly. Moreover, there is no particular need for providing a long narrow portion in a flow passage and no need for providing a discharge flow passage for exhalation discharge besides lead-out flow passage 104 for aerosol, so that the mouthpiece can be reduced in size as compared with the conventional ones. In addition, exhalation flowing into lead-out flow passage 104 can effectively be discharged from exhalation discharge openings 106, so that the necessity to provide an inhalation valve at pressure regulation opening 101 provided in the aerosol generation portion is reduced, allowing elimination of an inhalation valve.

Here, in a compressor-type inhaler, the flow rate of aerosol is relatively low as compared with an ultrasonic-type or ultrasonic-mesh-type inhaler. Also in this case, employment of the configuration described above can reliably prevent leakage of aerosol, which was confirmed by the present inventors.

Figure 13:
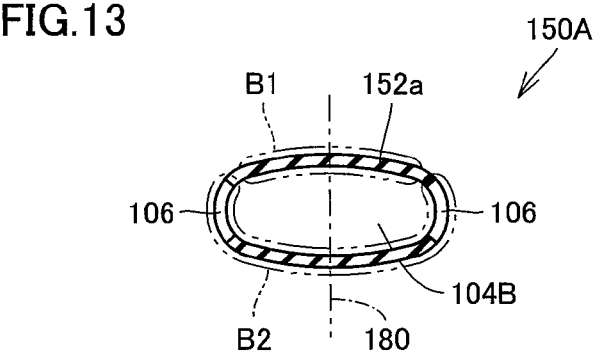
FIG. 13 is a cross-sectional view of the inhaler mouthpiece in the first embodiment of the present invention.

FIG. 13 is a cross-sectional view taken along line XIII-XIII in FIG. 8, of the inhaler mouthpiece in this embodiment as described above. As shown in FIG. 13, in inhaler mouthpiece 150A in the present embodiment, a pair of exhalation discharge openings 106 is provided at positions between which a plane 180 including the respective center lines of first flow passage portion 104A and second flow passage portion 104B is sandwiched, that is on the sides. This portion is at a position circumferentially displaced from that wall surface which crosses the center line of first flow passage portion 104A (that wall surface corresponding to a part surrounded by chained line B1 in FIG. 13), and is a part of a wall surface defining second flow passage portion 104B (the wall surface corresponding to a part surrounded by chained line B2 in FIG. 13). In inhaler mouthpiece 150A in the present embodiment, for the purpose of securing a large opening area of the exhalation discharge opening in order to discharge exhalation from lead-out flow passage 104 to the outside more reliably, a pair of exhalation discharge openings 106 is provided on the side surfaces of second flow passage portion 104B. However, the exhalation discharge opening may not necessarily be provided on the side portion and may be provided at any position as long as it is provided on the wall surface in the part surrounded by chained line B2 in FIG. 13.

(Second Embodiment)

Figure 14:
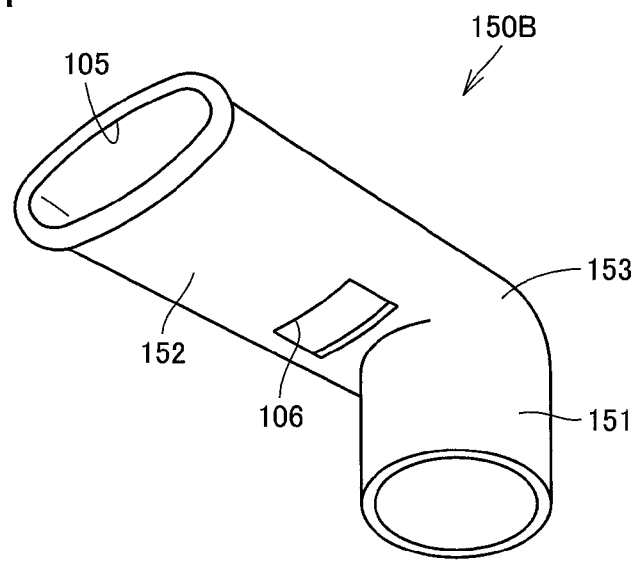
FIG. 14 is a perspective view of the inhaler mouthpiece in a second embodiment of the present invention.
Figure 15:
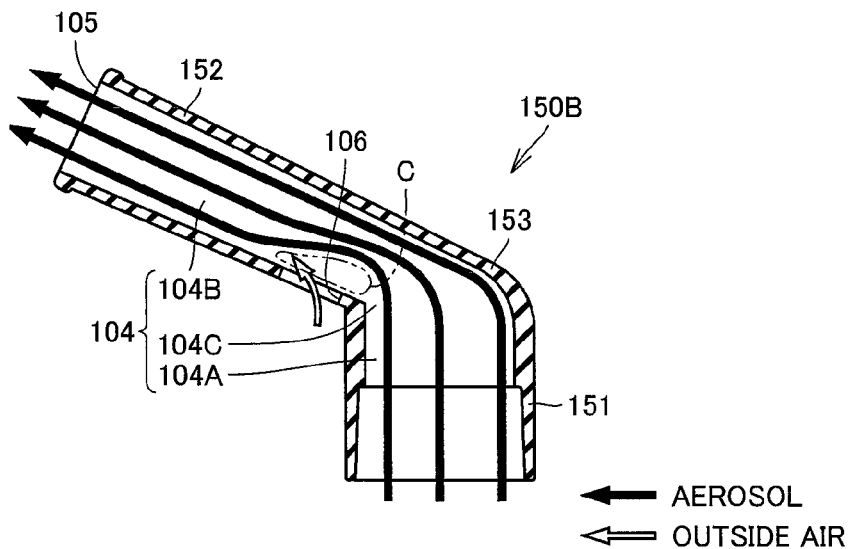
FIG. 15 is an illustration showing an airflow at a time of inhalation in the inhaler mouthpiece in the second embodiment of the present invention.
Figure 16:
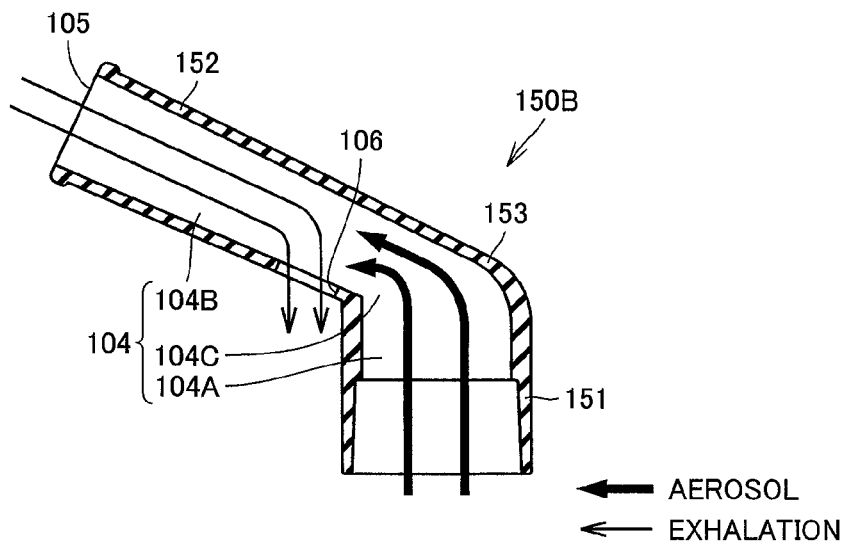
FIG. 16 is an illustration showing an airflow at a time of exhalation discharge in the inhaler mouthpiece in the second embodiment of the present invention.

FIG. 14 is a perspective view of an inhaler mouthpiece in a second embodiment of the present invention. FIG. 15 is an illustration showing an airflow at a time of inhalation in the inhaler mouthpiece in the present embodiment, and FIG. 16 is an illustration showing an airflow at a time of exhalation discharge. In the following, with reference to these figures, a structure of inhaler mouthpiece 150B in the present embodiment and an airflow formed therein will be described. It is noted that inhaler mouthpiece 150B in the present embodiment has a closely analogous structure to that of inhaler mouthpiece 150A in the first embodiment described above, and therefore in the figures the same parts will be denoted with the same reference characters and description thereof will not be repeated here.

As shown in FIG. 14 and FIG. 15, similar to inhaler mouthpiece 150A in the first embodiment as described above, inhaler mouthpiece 150B in the present embodiment is formed of a tubular member having lower-side tubular portion 151 and upper-side tubular portion 152 and has flow passage portion 104 inside thereof, including first flow passage portion 104A, second flow passage portion 104B and corner flow passage portion 104C. Then, at that wall of mouthpiece 150B defining corner flow passage portion 104C which crosses the center line of first flow passage portion 104A, curvature portion 153 is positioned which is formed by forming a curve that joins the wall defining first flow passage portion 104A and the wall defining second flow passage portion 104B to each other. In addition, at a position closer to corner flow passage portion 104C on the lower surface of mouthpiece 150B which defines second flow passage portion 104B, exhalation discharge opening 106 for discharging exhalation is provided. It is noted that a narrow portion is not particularly formed in inhaler mouthpiece 150B in the present embodiment.

In mouthpiece 150B configured as described above, the airflow in the case where the user puts mouthpiece 150B into the mouth to inhale aerosol is as shown in FIG. 15. Specifically, aerosol flowing in first flow passage portion 104A flows upward to reach corner flow passage portion 104C, flows along curvature portion 153, and thereafter passes through second flow passage portion 104B to be ejected from aerosol lead-out opening 105. Here, aerosol is smoothly introduced from first flow passage portion 104A to second flow passage portion 104B in the presence of curvature portion 153, so that the flow of aerosol is not disturbed in corner flow passage portion 104C.

Furthermore, since aerosol is collected at that wall surface of second flow passage portion 104B on which curvature portion 153 is formed, aerosol passes through a position further away from exhalation discharge opening 106 in the part where exhalation discharge opening 106 is provided. Therefore, a negative pressure is produced in the vicinity of the part where exhalation discharge opening 106 is provided (the part shown by region C in FIG. 15), to cause the outside air to be introduced from exhalation discharge opening 106, so that it is not likely that aerosol leaks out from exhalation discharge opening 106 thereby reliably preventing waste of aerosol.

On the other hand, at a time of exhalation discharge, exhalation introduced to second flow passage portion 104B of mouthpiece 150B by the user exhaling the breath is discharged from exhalation discharge opening 106 provided in second flow passage portion 104B to the outside, as shown in FIG. 16. Here, aerosol tends to flow into second flow passage portion 104B because of the feeding pressure of compressor 10. However, there is no fear that aerosol leaks out from exhalation discharge opening 106 since the flowing pressure of exhalation is usually larger. In addition, since a large part of exhalation is discharged from exhalation discharge opening 106 without flowing into first flow passage portion 104A, no exhalation flows into the interior space of case body 110 and therefore no aerosol leaks from pressure regulation opening 101.

Furthermore, in inhaler mouthpiece 150B configured as described above, the airflow in the case where the user confronts mouthpiece 150B to inhale aerosol ejected from mouthpiece 150B without putting mouthpiece 150B into the mouth is also approximately similar to the airflow at the time of inhalation in the case where the aforementioned user puts mouthpiece 150B into the mouth for inhalation. However, since a negative pressure is not developed inside case body 110 by the inhalation operation of the user, only compressed air sent from compressor 10 contributes to taking-in of the outside air and lead-out of aerosol so that aerosol is continuously ejected from aerosol lead-out opening 105 by the action of compressor 10. It is noted that in mouthpiece 150B in the present embodiment, here, leakage of aerosol is also effectively prevented, which mechanism is the same as that at a time of inhalation in the case where the aforementioned user puts mouthpiece 150B into the mouth for inhalation.

As described above, inhaler mouthpiece 150B as in the present embodiment can prevent aerosol from leaking out from exhalation discharge opening 106, irrespective of usage manners. Therefore, even without provision of an exhalation valve at exhalation discharge opening 106, the inhalation efficiency can be kept high, thereby reducing the number of components to drastically improve the operability at the time of cleaning and disinfection operations. In addition, the manufacturing costs can be reduced significantly. Moreover, there is no particular need for providing a narrow portion and no need for providing a discharge flow passage for exhalation discharge besides lead-out flow passage 104 for aerosol, so that the mouthpiece can be reduced in size as compared with the conventional ones. In addition, exhalation flowing in lead-out flow passage 104 can effectively be discharged from exhalation discharge opening 106, so that the necessity to provide an inhalation valve at pressure regulation opening 101 provided in the aerosol generation portion is reduced, allowing elimination of an inhalation valve.

(Third Embodiment)

Figure 17:
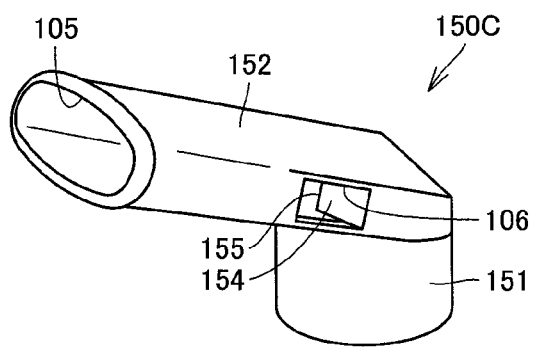
FIG. 17 is a perspective view of the inhaler mouthpiece in a third embodiment of the present invention.
Figures 18, 19, 20:
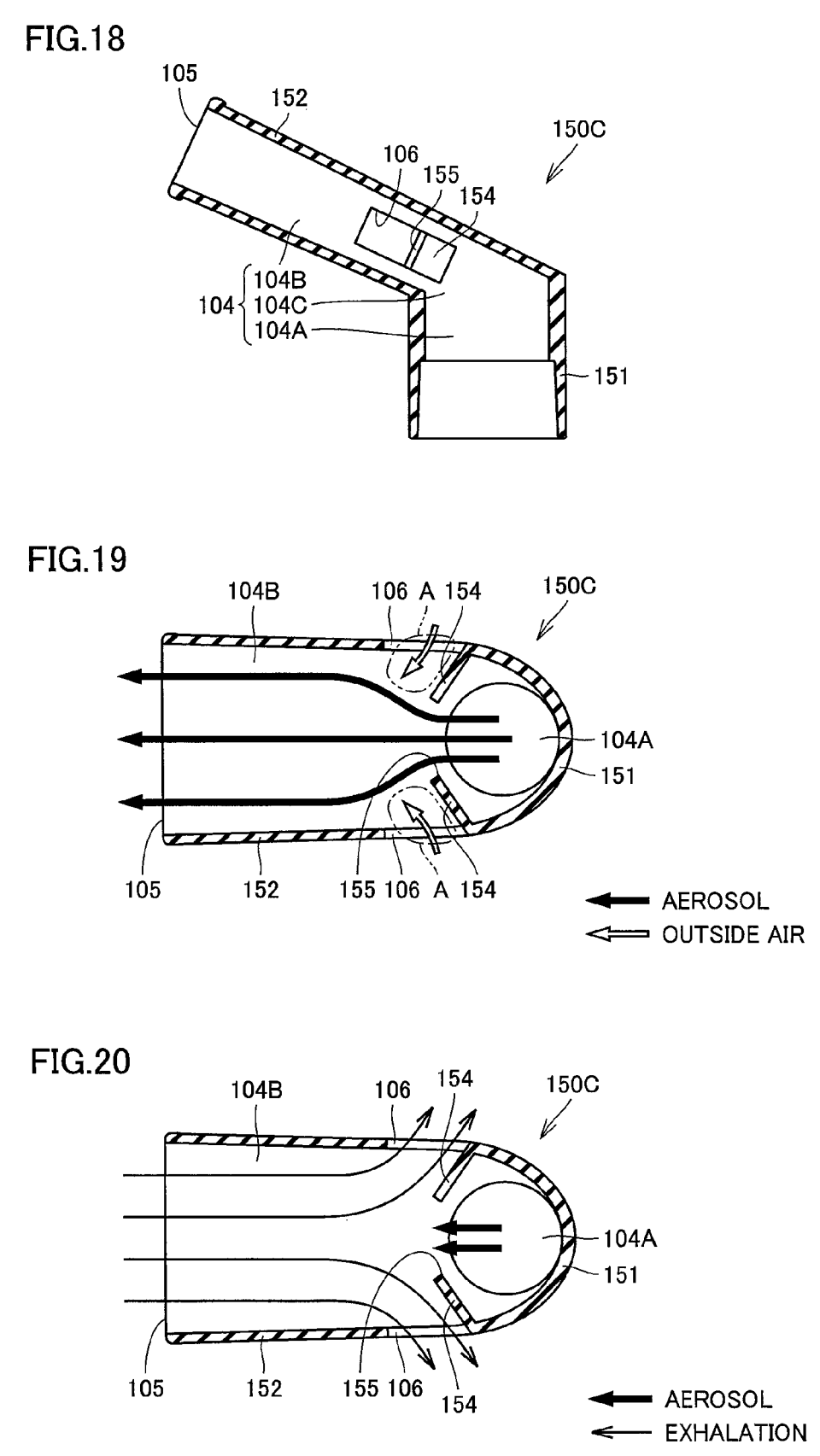

FIG. 17 is a perspective view of an inhaler mouthpiece in a third embodiment of the present invention, and FIG. 18 is a cross-sectional view. FIG. 19 is an illustration showing an airflow at a time of inhalation in the inhaler mouthpiece in the present embodiment, and FIG. 20 is an illustration showing an airflow at a time of exhalation discharge. In the following, with reference to these figures, a structure of inhaler mouthpiece 150C in the present embodiment and an airflow formed therein will be described. It is noted that inhaler mouthpiece 150C in the present embodiment has a closely analogous structure to that of inhaler mouthpiece 150A in the first embodiment described above, and therefore in the figures the same parts will be denoted with the same reference characters and description thereof will not be repeated here.

As shown in FIG. 17 and FIG. 18, similar to inhaler mouthpiece 150A in the first embodiment as described above, inhaler mouthpiece 150C in the present embodiment is formed of a tubular member having lower-side tubular portion 151 and upper-side tubular portion 152 and has flow passage portion 104 inside thereof, including first flow passage portion 104A, second flow passage portion 104B and corner flow passage portion 104C. However, unlike inhaler mouthpiece 150A in the first embodiment as described above, the part defining corner flow passage portion 104C is not provided with a curvature portion and has a flexed shape.

At a part closer to corner flow passage portion 104C on the opposite side surfaces of mouthpiece 150C which defines second flow passage portion 104B, narrow portions 154 which reduce the cross section of second flow passage portion 104B toward aerosol lead-out opening 105 are provided by flexing a part of the wall inwardly. A pair of narrow portions 154 is provided on opposite side surfaces of second flow passage portion 104B so that aerosol outflow opening 155 is formed at a part closer to the central position of second flow passage portion 104B. On the opposite side surfaces of upper-side tubular portion 152 at the positions corresponding to the parts where narrow portions 154 are provided, exhalation discharge openings 106 are respectively provided. Narrow portion 154 is positioned on the inner side than exhalation discharge openings 106, in the part of second flow passage portion 104B where exhalation discharge openings 106 are provided.

In mouthpiece 150C configured as described above, the airflow in the case where the user puts mouthpiece 150C into the mouth to inhale aerosol is as shown in FIG. 19. Specifically, aerosol flowing in first flow passage portion 104A flows upward to reach corner flow passage portion 104C, flows into second flow passage portion 104B, and is thereafter ejected from aerosol lead-out opening 105.

Here, since aerosol is collected to the upper surface side of the flow passage wall defining second flow passage portion 104B, aerosol passes through a position further away from exhalation discharge openings 106 in the part where exhalation discharge opening 106 is provided. Therefore, a negative pressure is produced in the vicinity of the part where exhalation discharge openings 106 are provided (the part shown by region A in FIG. 19), to cause the outside air to be introduced from exhalation discharge opening 106, so that it is not likely that aerosol leaks out from exhalation discharge opening 106 thereby reliably preventing waste of aerosol.

On the other hand, at a time of exhalation discharge, exhalation introduced to second flow passage portion 104B of mouthpiece 150C by the user exhaling the breath is discharged from exhalation discharge openings 106 provided in second flow passage portion 104B to the outside, as shown in FIG. 20. Here, aerosol tends to flow into second flow passage portion 104B because of the feeding pressure of compressor 10. However, there is no fear that aerosol leaks out from exhalation discharge openings 106 since the flowing pressure of exhalation is usually larger. In addition, since a large part of exhalation is discharged from exhalation discharge openings 106 without flowing into first flow passage portion 104A through aerosol outflow opening 155, no exhalation flows into the interior space of case body 110 and therefore no aerosol leaks from pressure regulation opening 101.

Furthermore, in inhaler mouthpiece 150C configured as described above, the airflow in the case where the user confronts mouthpiece 150C to inhale aerosol ejected from mouthpiece 150C without putting mouthpiece 150C into the mouth is also approximately similar to the airflow at the time of inhalation in the case where the aforementioned user puts mouthpiece 150C into the mouth for inhalation. However, since a negative pressure is not developed inside case body 110 by the inhalation operation of the user, only compressed air sent from compressor 10 contributes to taking-in of the outside air and lead-out of aerosol so that aerosol is continuously ejected from aerosol lead-out opening 105 by the action of compressor 10. It is noted that in mouthpiece 150C in the present embodiment, here, leakage of aerosol is also effectively prevented, which mechanism is the same as that at a time of inhalation in the case where the aforementioned user puts mouthpiece 150C into the mouth for inhalation.

As described above, inhaler mouthpiece 150C as in the present embodiment can prevent aerosol from leaking out from exhalation discharge opening 106, irrespective of usage manners. Therefore, even without provision of an exhalation valve at exhalation discharge openings 106, the inhalation efficiency can be kept high, thereby reducing the number of components to drastically improve the operability at the time of cleaning and disinfection operations. In addition, the manufacturing costs can be reduced significantly. Moreover, there is no particular need for providing a long narrow portion in a flow passage and no need for providing a discharge flow passage for exhalation discharge besides lead-out flow passage 104 for aerosol, so that the mouthpiece can be reduced in size as compared with the conventional ones. In addition, exhalation flowing into lead-out flow passage 104 can effectively be discharged from exhalation discharge openings 106, so that the necessity to provide an inhalation valve at pressure regulation opening 101 provided in the aerosol generation portion is reduced, allowing elimination of an inhalation valve.

Although, in the first to third embodiments as described above, a compressor-type inhaler has been described as an illustrative example of inhaler, the application of the present invention is not limited thereto and the present invention may be applied to an ultrasonic-type inhaler or an ultrasonic-mesh-type inhaler.

In this manner, the embodiments disclosed herein are illustrative in all respects and are not limitative. The technical scope of the present invention is defined by the claims and equivalencies to the claims and all modifications within the scope of the claims are embraced herein.

The invention claimed is:

1. An inhaler comprising an apparatus body and a compressor for sending compressed air and for generating aerosol inside said apparatus body and supplying the aerosol to outside of said apparatus body to allow a user to inhale the aerosol, said apparatus body including an aerosol generation portion including a reservoir portion storing liquid and an atomization portion atomizing liquid stored in said reservoir portion into spray particles and applying the atomized spray particles to outside air introduced into said apparatus body, and an aerosol lead-out portion;

wherein said aerosol lead-out portion comprises:

a lower tubular portion connected to said aerosol generation portion, extending in a first direction and defining a first flow passage portion;

an upper tubular portion with an aerosol lead-out opening leading aerosol generated in said aerosol generation portion to outside and extending in a second direction different from said first direction and defining a second flow passage portion; and a corner flow passage portion, located between the lower tubular portion and the upper tubular portion, said lower tubular portion, said upper tubular portion and said corner flow passage portion together forming a lead-out flow passage consisting of said first flow passage portion, said second flow passage portion and said corner flow passage portion for leading aerosol generated in said aerosol generation portion to outside through said aerosol lead-out opening without passing through any valve;

a pair of exhalation discharge openings having no valves in side walls of said upper tubular portion proximal to said corner flow passage portion and mutually facing and unblocked from each other, and first and second narrowing walls that reduce the cross section of the second flow passage portion, each of the first and second narrowing walls extending obliquely from opposing inner side surfaces of the upper tubular portion proximate the exhalation discharge openings, wherein the first and second walls each have a first end positioned on opposite ones of the opposing inner side surfaces and a second free end, wherein the second free ends of the first and second walls mutually face and are spaced from each other to form an aerosol outflow opening in the second flow passage of reduced cross section than the second flow passage portion, wherein the first and second walls are shaped to direct exhaled air to the exhalation discharge openings.

2. The inhaler according to claim 1, wherein said aerosol generation portion further includes a pressure regulation opening for regulating an internal pressure of said apparatus body, said aerosol generation portion communicating continuously without passing through any valve with space outside said aerosol lead out portion, and a passage at a part extending from said pressure regulation opening to said atomization portion has its cross section reduced so that flow resistance is higher at a particular part than at other parts of the passage, and includes a labyrinth-like part bent at least once.

3. The inhaler according to claim 1, wherein said aerosol lead-out portion is removably attached to said aerosol generation portion.

4. The inhaler according to claim 1, wherein said compressor sends said compressed air by blowing on a baffle provided in said atomization portion such that said liquid stored in said reservoir portion is caught up in the blown compressed air and thereby becomes atomized into spray particles.

5. An inhaler mouthpiece removably attached to an aerosol generation portion of an inhaler for leading aerosol generated in said aerosol generation portion to outside, comprising:

a lower tubular portion connected to said aerosol generation portion, extending in a first direction and defining a first flow passage portion;

an upper tubular portion with an aerosol lead-out opening leading aerosol generated in said aerosol generation portion to outside and extending in a second direction different from said first direction and defining a second flow passage portion; and a corner flow passage portion located between the lower tubular portion and the upper tubular portion, said lower tubular portion, said upper tubular portion and said corner flow passage portion together forming a lead-out flow passage consisting of said first flow passage portion, said second flow passage portion and said corner flow passage portion for leading aerosol generated in said aerosol generation portion to outside through said aerosol lead-out opening without passing through any valve;

a pair of exhalation discharge openings having no valves in side walls of said upper tubular portion proximal to said corner flow passage portion and mutually facing and unblocked from each other, and first and second narrowing walls that reduce the cross section of the second flow passage portion, each of the first and second narrowing walls extending obliquely from opposing inner side surfaces of the upper tubular portion proximate the exhalation discharge openings, wherein the first and second walls each have a first end positioned on opposite ones of the opposing inner side surfaces and a second free end, wherein the second free ends of the first and second walls mutually face and are spaced from each other to form an aerosol outflow opening in the second flow passage of reduced cross section than the second flow passage portion, wherein the first and second walls are shaped to direct exhaled air to the exhalation discharge openings.

* * * * *